United States Patent [19]

Nishimura et al.

[11] Patent Number: 5,495,105
[45] Date of Patent: Feb. 27, 1996

[54] METHOD AND APPARATUS FOR PARTICLE MANIPULATION, AND MEASURING APPARATUS UTILIZING THE SAME

[75] Inventors: Matsuomi Nishimura, Ohmiya; Kazuo Isaka, Tokyo; Tadashi Okamoto; Kazumi Tanaka, both of Yokohama; Toshikazu Onishi, Tokyo; Takeshi Miyazaki, Ebina; Hidehito Takayama, Chigasaki, all of Japan

[73] Assignee: Canon Kabushiki Kaisha, Tokyo, Japan

[21] Appl. No.: 375,253

[22] Filed: Jan. 19, 1995

Related U.S. Application Data

[63] Continuation of Ser. No. 17,390, Feb. 12, 1993, abandoned.

[30] Foreign Application Priority Data

Feb. 20, 1992 [JP] Japan .................. 4-033441
Feb. 24, 1992 [JP] Japan .................. 4-036262
Dec. 24, 1992 [JP] Japan .................. 4-344578

[51] Int. Cl.$^6$ .......................... G01B 13/00; G01N 11/00
[52] U.S. Cl. .................. 250/251; 356/39; 356/335; 356/343; 356/338; 250/222.2
[58] Field of Search ........................ 356/335, 336, 356/337, 338, 339, 340, 341, 342, 343, 251, 441, 39, 38; 250/222.2, 251

[56] References Cited

U.S. PATENT DOCUMENTS

| | | | |
|---|---|---|---|
| 3,710,279 | 1/1973 | Ashkin | 250/281 |
| 3,808,550 | 4/1974 | Ashkin | 331/94.5 |
| 4,723,129 | 2/1988 | Endo et al. | 346/1.1 |
| 4,740,796 | 4/1988 | Endo et al. | 346/1.1 |
| 4,887,721 | 12/1989 | Martin et al. | 209/579 |
| 5,198,369 | 3/1993 | Itoh et al. | 356/38 |

FOREIGN PATENT DOCUMENTS

| | | |
|---|---|---|
| 0091545 | 3/1990 | Japan . |
| 0191318 | 8/1991 | Japan . |
| 0223645 | 10/1991 | Japan . |

OTHER PUBLICATIONS

Laser–Scanning Micromanipulation and Spatial Patterning of Fine Particles by Keiji Sasaki, Masanori Koshioka, Hiroaki Misawa, Noboru Kitamura and Hiroshi Masuhara, Japanese Journal of Applied Physics, vol. 30, No. 5B, May 1991, pp. L907–L909.

Optical Trapping of a metal particle and a water droplet by a scanning laser beam, by Keiji Sasaki, Masanori Koshioka, Hiroaki Misawa, and Noboru Kitamusa, Appl. Phys. Lett. 60 (7), Feb. 17, 1992, American Institute Physics.

*Primary Examiner*—Robert P. Limanek
*Assistant Examiner*—Alexander Oscar Williams
*Attorney, Agent, or Firm*—Fitzpatrick, Cella, Harper & Scinto

[57] ABSTRACT

A flow of liquid containing floating fine particles is formed in a flow path, thereby causing successive movement of the particles. A light beam having intensity distribution from a laser is focused on the liquid flow, whereby the particle is optically trapped at the irradiating position, thus being stopped against the liquid flow or being slowed by a braking force. This phenomenon is utilized in controlling the spacing of the particles in the flow or in separating the particles.

7 Claims, 10 Drawing Sheets

FIG. 4A
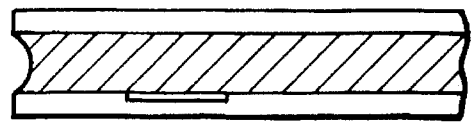
FIG. 4B
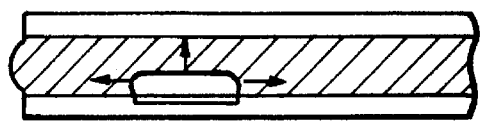
FIG. 4C
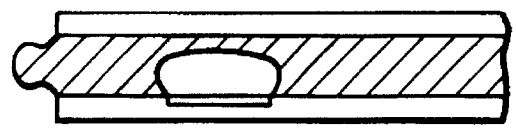
FIG. 4D
FIG. 4E
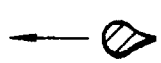 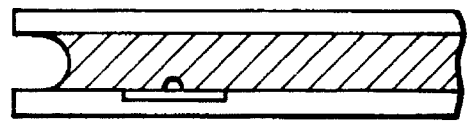

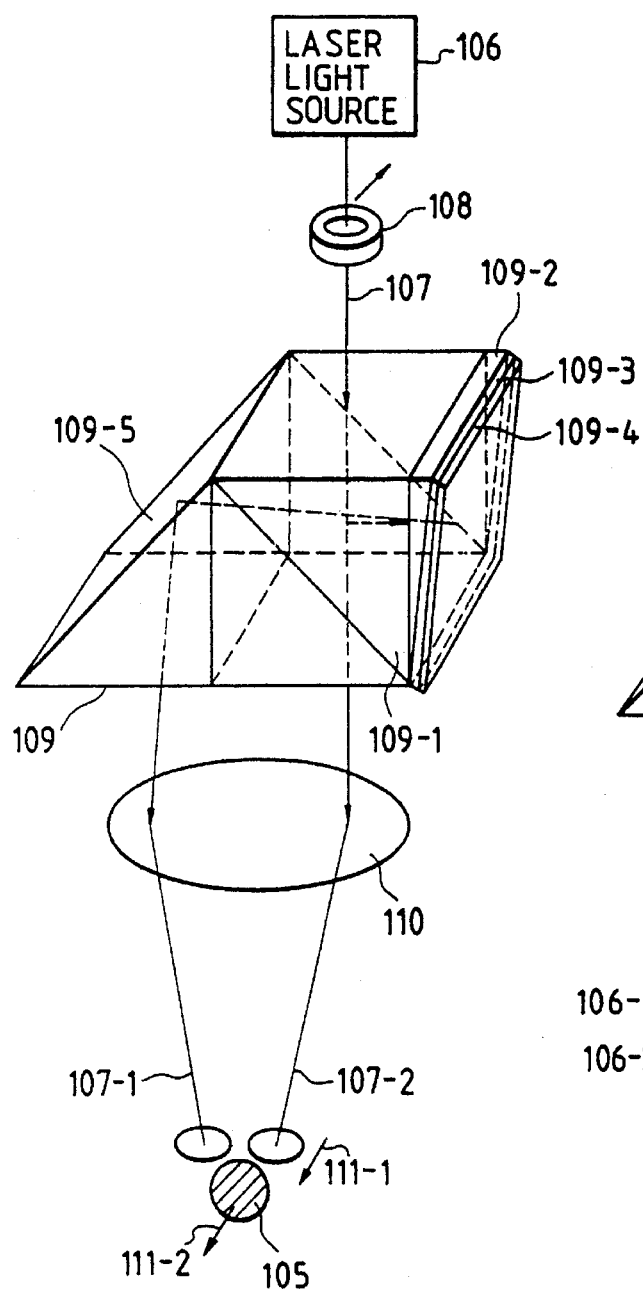
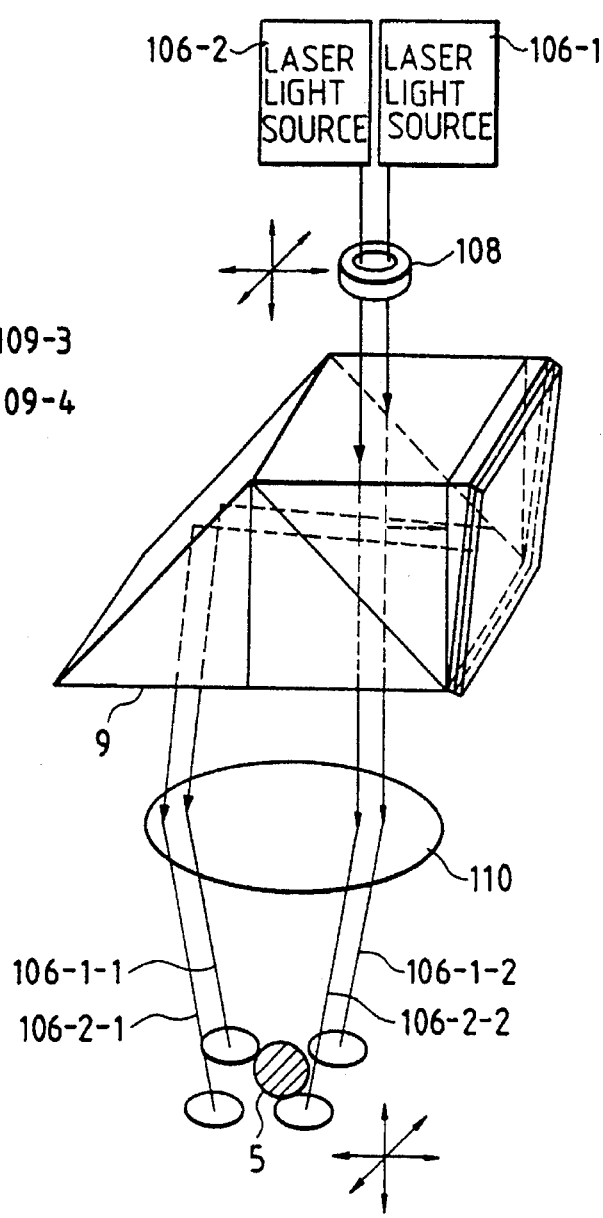

METHOD AND APPARATUS FOR PARTICLE MANIPULATION, AND MEASURING APPARATUS UTILIZING THE SAME

This application is a continuation of application Ser. No. 08/017,390 filed Feb. 12, 1993, now abandoned.

BACKGROUND OF THE INVENTION

1. Field of the Invention

The present invention relates to a technology for manipulating movement of particles in a medium.

2. Related Background Art

The sheath flow method is already well known for transporting fine particles dispersed in a medium such as liquid, in linear array, one by one. In this method, at the center of a high-speed sheath liquid flow, there is formed a very fine flow of liquid in which fine particles such as blood cells, viruses, microorganisms or carrier particles (such as latex particles or ceramic particles) are suspended, whereby the fine particles are separated one by one, transported in linear array. Such sheath flow method is applied to so-called flow cytometry which is used for counting the number of such fine particles by an optical or electrical method or for identifying the sort or property of such particles by statistical processing of a number of thus obtained data.

On the other hand, for classifying the fine particles by size or specific gravity thereof, there are known methods utilizing centrifugal force or sieving means such as meshes or gels. These methods are applied to classify copying toner or other industrial particles, or to separate microorganisms, cells or the like.

Apart from these technologies, it is already known that, when fine particles are irradiated with a light beam, which has an intensity gradient such as Gaussian laser beam, the particles are subjected to scattering and gradient forces of radiation pressure so that the fine particles are moved in the direction of irradiation by an axial force and are trapped in the light beam by a radial force. This is a technology called optical trapping, disclosed, for example, in Japanese Patent Laid-Open Application Nos. 2-91545 and 3-223645 and in U.S. Pat. No. 3,808,550. Also, U.S. Pat. No. 4,887,721 discloses a method of switching two crossing laser beams, thereby transporting the fine particles to a predetermined position by laser optical pressure.

SUMMARY OF THE INVENTION

In consideration of the foregoing, the present invention is to provide a novel method for manipulating particles in a medium. A more specific object of the present invention is to provide a novel method and apparatus for continuously transporting particles in an array with a desired interval. Another more specific object of the present invention is to provide a novel method and apparatus for separating particles that differ in size or in refractive index.

BRIEF DESCRIPTION OF THE DRAWINGS

FIGS. 4A to 4E are views showing the mode of a function of micropump;

FIG. 11 is a schematic view of a ninth embodiment;

FIG. 12 is a schematic view of a tenth embodiment;

DETAILED DESCRIPTION OF THE PREFERRED EMBODIMENTS

[1st embodiment]

Figure 1:
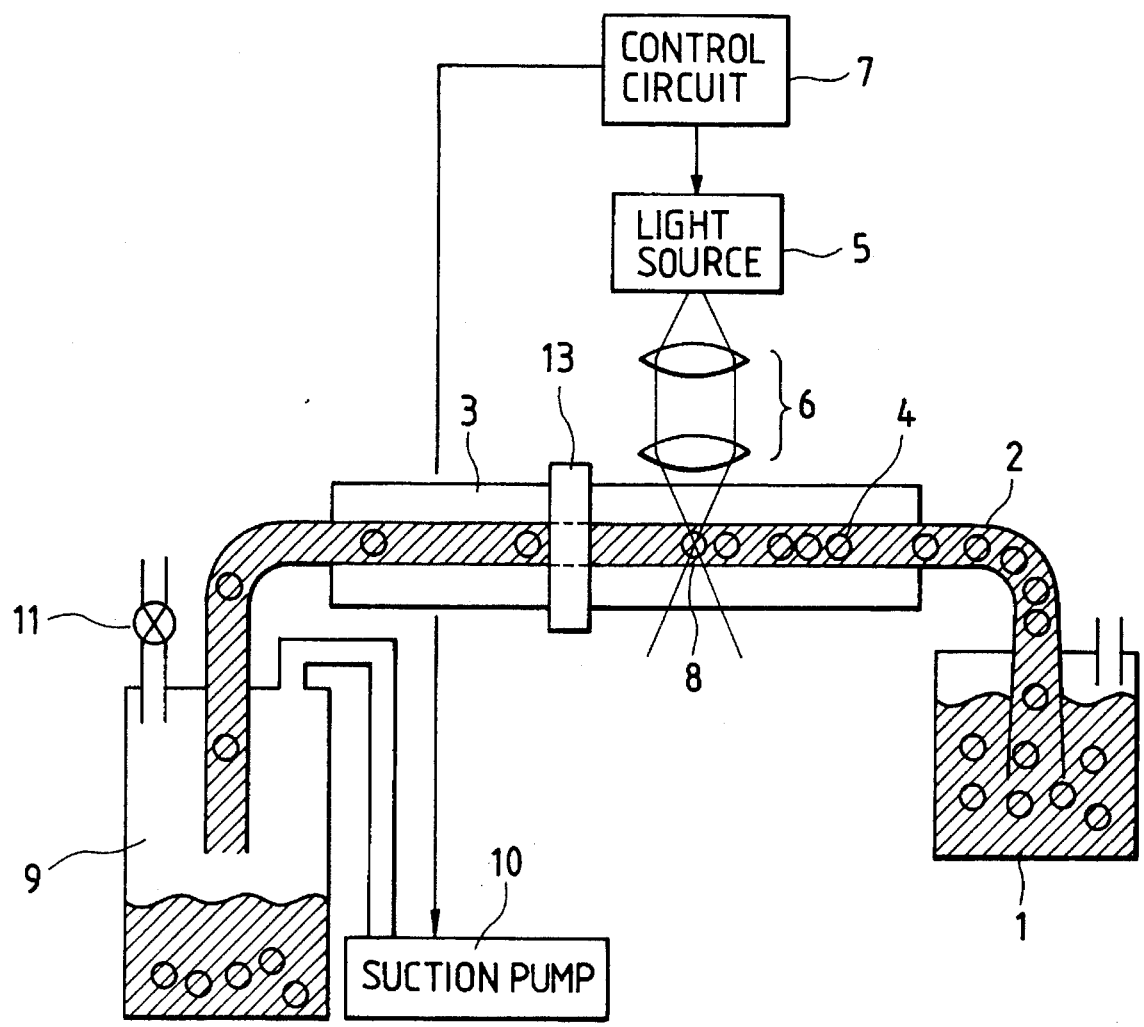
FIG. 1 is a view showing the configuration of an apparatus constituting a first embodiment of the present invention.

FIG. 1 is a view showing the configuration of an apparatus constituting a first embodiment of the present invention, wherein a supply container 1 contains therein a dispersion of fine particles, consisting of a plurality of fine particles (for example, blood cells, viruses, microorganisms, bioparticles such as DNA or RNA, carrier particles or industrial particles) and a dispersion medium. The fine particles and the dispersion medium have comparable specific gravities. In the embodiment the fine particles are latex particles of a given size while the dispersion medium is water. The supply container 1 is connected to a flow path 2, which is provided with a flow cell 3 of quartz glass in the middle and connected to a discharge container 9. A vacuum pump 10 and a valve 11 are connected to the discharge container 9. The vaccum pump 10 is constantly operated to generate a low pressure in the discharge container 9, thereby creating a flow of particle dispersion of a constant velocity in the flow path 2. The fine particles 4 in the dispersion medium move together with the flow. The internal diameter of the flow path 2 has to be larger than the diameter of the largest particle, but preferably does not exceed twice of the diameter of the largest particle, since an excessively large internal diameter increases the possibility of simultaneous flowing of plural particles.

A light source 5, positioned above the flow cell 3, generates a light beam of a predetermined intensity gradient for optical trapping, and is so selected that the wavelength thereof is in a low optical absorption band of the particles. In the present embodiment there is employed a $TEM_{00}$ mode of YAG laser to generate a Gaussian beam, but there may also be employed various lasers such as a solid-state laser, a gas laser or semiconductor laser, or light sources not limited to laser, which capable of generating light having an intensity gradient. The light beam emitted by the light source 5 is focused by a lens system 6 to a position 8 in the flow path in the flow cell 3. A control means 7 controls the light source 5 itself or light control means (such as a shutter or a light modulating element) separate from the light source 5, thereby effecting on-off control or intensity modulation of the light irradiation on the irradiation position 8. The control means 7 also sends instruction to the vacuum pump 10. At a downstream side of the irradiation position 8 in the flow cell 3, there is provided particle measuring means 13 utilizing, for example, optical, electrical, magnetic or acoustooptical method.

When the fine particle passes the irradiation position 8 while the light beam is focused thereon, the fine particle is subjected to two forces, namely, an axial force toward the irradiating direction of the light beam, and a radial force to confine the particle in the optical axis. Each of the forces depends on the intensity of the laser beam and the intensity distribution along the optical axis, namely, degree of condensation by the lens and the intensity distribution in a direction perpendicular to the optical axis. They also depend on the refractive index and absorbance (reflectance) of the particle, and on the particle size. By means of the radial force, the fine particle may be stopped by trapping at the irradiation position 8, or the moving velocity of the particle may be temporarily reduced close to zero. The fine particle is not subjected to such forces when the light irradiation is not conducted, and moves together with the flow of the dispersion medium. Consequently, the irradiation of the light beam is repeated by turning on and off at a constant interval under the control of the control means (for example, the light beam on for 1 second and off for 0.1 seconds), whereby gate function with constant period can be applied to the moving fine particles. Thus, the fine particles can be moved with a desired constant spacing in the flow path behind the irradiating position 8.

More specifically, if the concentration of the fine particles in the dispersion medium is high or if the flow velocity is large, the fine particles move in succession from the supply container 1 to the irradiating position 8 as shown in FIG. 1. In such condition, the period of off-irradiation (in which the particle can pass) is made shorter than the period of on-irradiation (trapping period), so that a plurality particles do not pass through the irradiating position at a time. On the other hand, in the case contrary to the above-mentioned condition, there is one trapping conducted for a long time to accumulate a plurality of particles in front of the trapping position, and then the beam is turned on and off as explained above, thereby transferring the particles at a constant spacing.

Also, since the flow velocity of the dispersion medium is always constant, the spacing of the fine particles in movement may be arbitrarily varied by a variation in the cycle time of the light irradiation. In the condition of the off-irradiation, the irradiating light intensity need not necessarily be brought to zero, but may be reduced to a level not causing the particle trapping.

It is also possible to discriminate whether the fine particle is trapped at the irradiation position 8, by monitoring the light amount with a photosensor system positioned opposite to the light source 5 across the flow cell 3. Also, more reliable control is possible by determining the timing of irradiation, based on the monitoring.

In the case where the fine particles are of a lower refractive index than that of the surrounding medium or are reflecting or absorbing the light, the trapping may be conducted by the methods explained in the eighth and subsequent embodiments.

[2nd embodiment]

Figure 2:
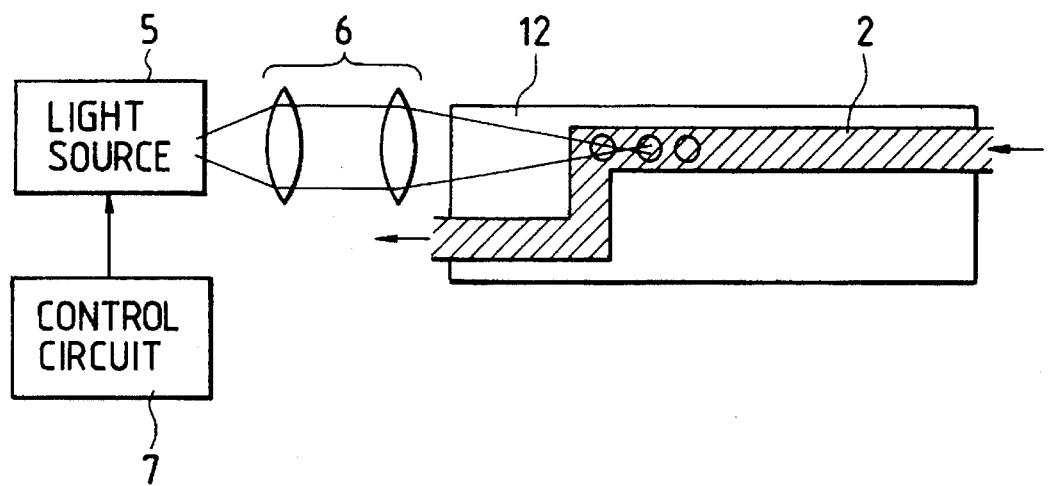
FIG. 2 is a view showing a part of the configuration of an apparatus of a second embodiment.

FIG. 2 illustrates the configuration of a part of the apparatus of a second embodiment of the present invention, which is a partial modification of the embodiment shown in FIG. 1 and in which non-illustrated components are the same as those in FIG. 1.

In FIG. 2, the flow path 2 in a flow cell 12 is bent in a key-shape, and the light for optically trapping is irradiated on the flow path in front of the bent portion, in a direction along the flow path. In contrast to the foregoing embodiment in which the light irradiation is made laterally to the flow of the fine particles to trap the particle by the radial force generated by the light irradiation, the present embodiment effects the light irradiation in a direction opposite to the flow of the fine particles, thereby trapping the particle by both the axial and radial forces.

In the case where the fine particles are of a lower refractive index than the surrounding medium, or are reflecting or absorbing the light, the trapping may be achieved by methods explained in the eighth and subsequent embodiments.

[3rd embodiment]

Figure 3:
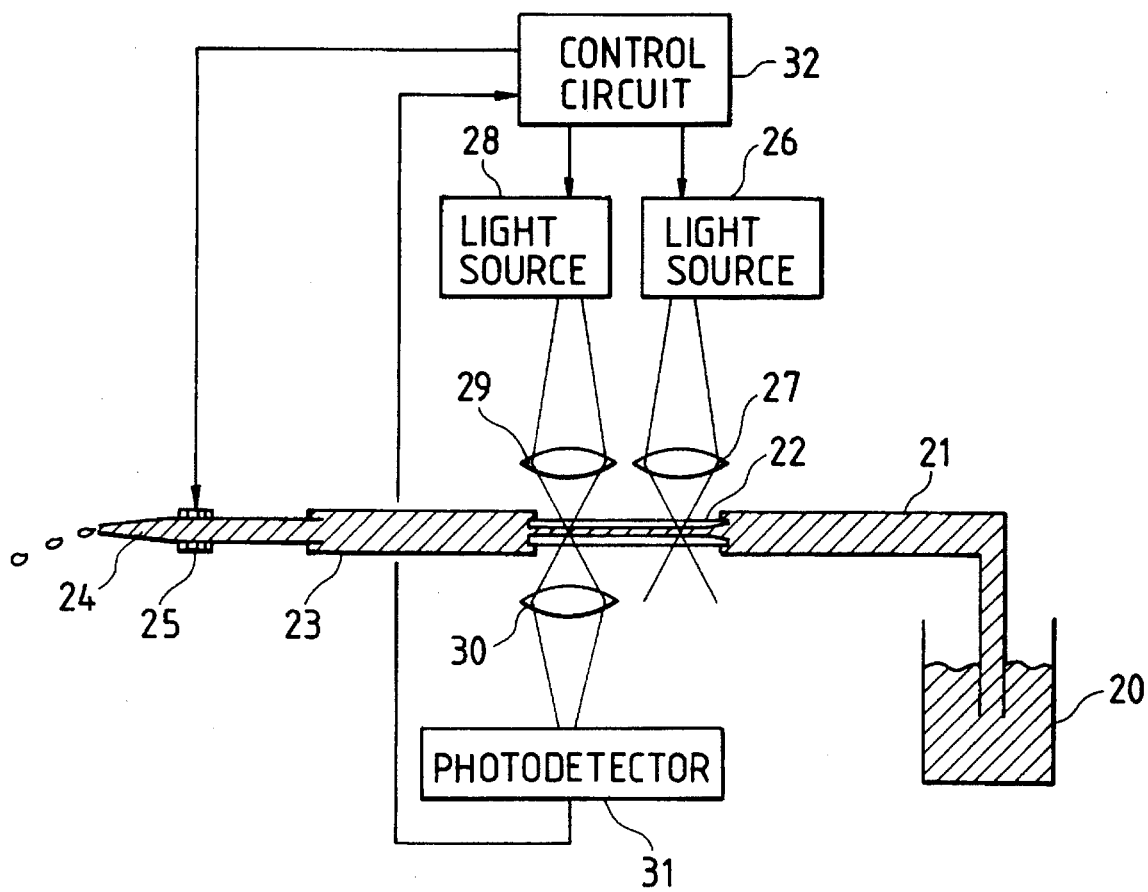
FIG. 3 is a view showing the configuration of an apparatus of a third embodiment.

FIG. 3 shows the configuration of an apparatus constituting a third embodiment of the present invention. A supply container 20 contains particle dispersion in which a number of fine particles float in a dispersion medium. In the supply container 20 there is immersed an end of a silicone tube 21, of which the other end is connected to a flow cell 22 of quartz glass. The flow cell 22 is in turn connected to a silicone tube 23, of which the other end is connected to a nozzle 24 equipped with a micropump 25, to be explained below.

As means for forming a flow of the dispersion medium there is employed a pump, which can be exemplified by a vacuum pump for sucking the dispersion medium from the side of the discharge container, a pressure pump for pressurizing the dispersion medium from the side of the supply container, or a feed pump having a liquid feeding mechanism. Although the vacuum pump is employed in the first embodiment, the present embodiment employs a micropump constituting a feed pump. More specifically, the micropump includes a heat-generating element. When a pulse voltage is given to the heat-generating element, the liquid heated by the generated heat is gasified instantaneously to generate a bubble, and liquid drops are discharged from the nozzle 24 by a pressure generated by the impact due to expansion or contraction of the bubble. The particle dispersion is sucked in toward the nozzle, corresponding to the amount of such discharge. A feeding action on the particle dispersion is obtained by effecting the discharge in consecutive manner with a high frequency to form a flow in the flow cell 22. The fine particles move together with the flow.

FIGS. 4A to 4E illustrate the mode of liquid droplet discharged by bubble generation. When the heat-generating element is heated instantaneously by a pulse voltage in an initial State shown in FIG. 4A, the liquid in the vicinity of the element is gasified to generate a bubble as shown in FIG. 4B. Then, due to a volume expansion corresponding to the gasification, the liquid in the vicinity of the nozzle aperture is pushed out from the aperture as shown in FIG. 4C. The bubble originally expanding starts to contract by cooling as shown in FIG. 4D, and the liquid pushed out from the aperture forms a liquid droplet and flies in the air as shown in FIG. 4E, because of the volume contraction. The liquid is replenished by capillary phenomena, corresponding to the discharged volume, whereby the initial state shown in FIG. 4A is restored. The basic principle of the liquid droplet discharging by bubble formation is detailedly described, for example, in U.S. Pat. Nos. 4,723,129 and 4,740,796.

As another embodiment of the micropump, it is also possible to replace the heat-generating element with a piezoelectric element and to apply an electric pulse thereto, thereby emitting a liquid droplet by a pressure generated by the impact due to volume change of the piezoelectric element. In such case there is preferred a cylindrical piezoelement which is so provided as to surround the flow path.

The liquid feeding ability of the micropump can be selected by the voltage and frequency of the electric pulse given to the heat-generating element or the piezoelectric element. In the present embodiment the voltage and frequency supplied to the micropump 25 are so selected as to obtain a flow of the velocity in the order of 200 µm/sec. in the flow path of the flow cell 22.

Again referring to FIG. 3, a light source 26 is composed of a YAG laser (1064 nm) for providing the fine particle with axial and radial forces, and the light for trapping the particle is condensed by a lens system 27 onto the flow path in the flow cell 22. Another light source 28 is composed of an $Ar^+$ laser (488 nm) for measuring the optical characteristics of the fine particle, and the light for particle measurement is focused by a lens system 29 onto the flow path in the flow cell 22. The light emitted from the fine particle irradiated by the lens system 29 is collected by a lens system 30 and received by a photodetector 31 (photomultiplier or photodiode). A control means 32 effects the control of the light sources 26, 28, the analysis of the particle by the output from the photodetector 31, and the driving of the micropump 25.

When the light source 26 is turned on and the light thereof is focused on the flow path, the fine particles moving in the flow path can be trapped against the flow. When the light source is turned off, the trapping is released and the fine particle moves again together with the flow. It is therefore possible, as in the foregoing embodiments, to control the spacing of the fine particles separately flowing one by one in the flow path, by turning on and off the irradiation of the light source 26 with a suitable interval corresponding to the flow velocity and the concentration of the fine particles, under the control of the control means 32. The fine particles flowing in such array pass the irradiation position of the light source 28 in succession, and the light emitted from each particle (scattered, transmitted or fluorescent light) upon such passing is detected by the photodetector 31. The detected data are fetched by the control means 32, which effects the analysis such as the identification of sort and property of the particles, based on the data obtained from a plurality of particles.

In the case where the fine particles are of a lower refractive index than the surrounding medium, or are reflecting or absorbing the light, the trapping may be made by methods of eighth and subsequent embodiments to be explained later.

[4th embodiment]

Figure 5:
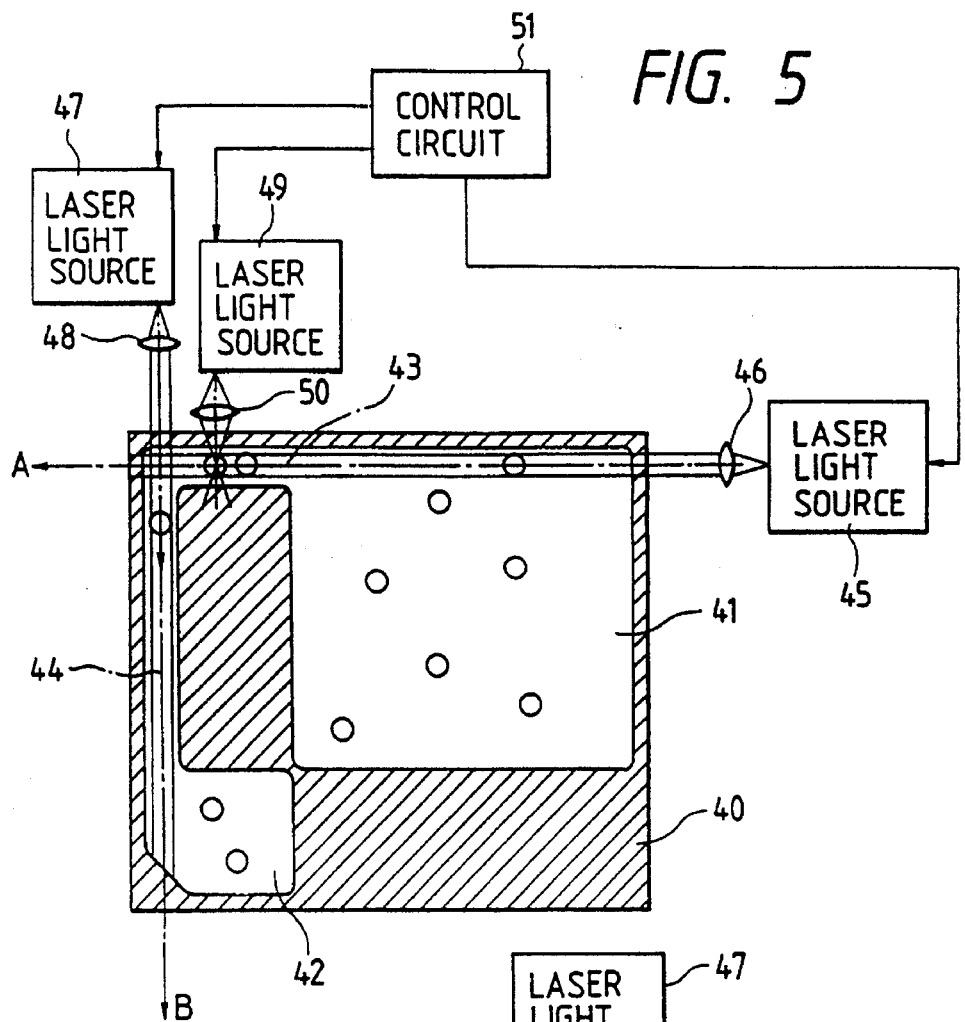
FIG. 5 is a view showing the configuration of an apparatus of a fourth embodiment.

FIG. 5 illustrates the configuration of an apparatus constituting a fourth embodiment of the present invention, in which the particle movement is achieved by the radiation pressure instead of the pump.

Referring to FIG. 5, in a cell 40 of a transparent material such as glass or plastic, there are formed a first resorvoir 41 and a second reservoir 42, which are mutually connected by paths 43, 44. Each of the paths 43, 44 has a square cross section, of which size is selected larger than the maximum diameter of a plurality of particles, but smaller than twice of the maximum diameter.

There are provided three independent laser light sources 45, 47, 149 as illustrated, and lens systems 46, 48, 50 are provided respectively, corresponding to the laser light sources. Laser beams emitted from the laser light sources 45, 47 are converted, respectively by the lens systems 46, 48, into parallel light beams (called first and second laser beams). An axial force is applied by the laser beams on the fine particles present in the light beams, in the directions of incidence of the laser beams, thereby moving the fine particles along the optical axes. Since the first and second laser beams have Gaussian intensity distribution, there can be obtained an effect that the fine particle once caught in the light beam is attracted to the optical axis by the radial force and is not released from the light beam. The first laser beam irradiating the path 43 crosses the second laser beam irradiating the path 44, and, at the crossing point, the radiation pressure of the second light beam is set larger than that of the first laser beam, so that the fine particles moved by the radiation pressure are smoothly moved from the path 43 to the path 44.

On the other hand, the laser beam emitted from the laser light source 49 is converted, by the lens system 50, into a converging light beam (called third laser beam) condensed on the path 43, thereby providing the fine particle with a radial force for particle trapping, against the axial force of the first laser beam from the laser light source 45. In the present embodiment the third laser beam is irradiated on a position in front of the crossing point of the first and second light beams, but the third light beam may also be irradiated on the crossing point of the first and second light beams.

Figure 6:
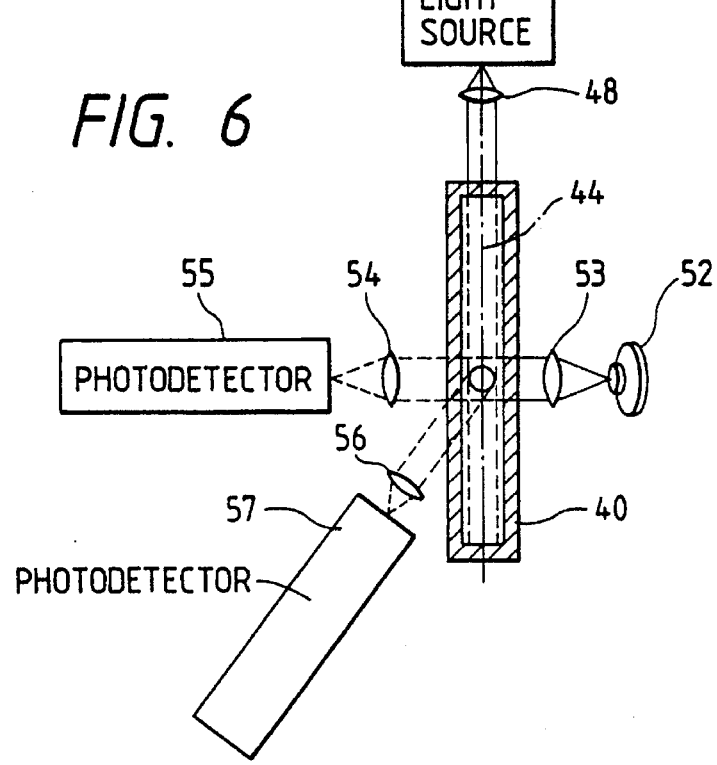
FIG. 6 is a view showing the configuration of a measuring system in the apparatus shown in FIG. 5.

In the path 44 there is provided a measuring system as shown in FIG. 6, which is a view seen from the left-hand side of FIG. 5. The measured system includes, for effecting measuring light irradiation on the individually moving fine particles, a light source 52 (such as laser light source, halogen light source or xenon light source) and a lens system 53. Among the lights emitted from the irradiated fine particle, the scattered light is detected by a lens 54 and a photodetector 5 while the fluorescent light is detected by a lens 56 and a photodetector 57. The outputs from the photodetectors 55, 57 are fetched by the control means 51 for the calculation for particle analysis.

When a fine particle dispersed in the first reservoir 41 enters within the first laser beam, it is caught in the light beam and is transported in a direction A. It is thus guided to the path 43 and reaches the focused position of the third laser beam. When the irradiation of the third laser beam is turned on, the fine particle stops by trapping it with the light beam. When the irradiation is turned off, the trapping force is removed, whereby the fine particle starts to move again in the direction A, under the axial force by the first laser beam. When the fine particle reaches the crossing point of the first and second laser beams, it starts to move in a direction B under the stronger radiation pressure of the second laser beam, and reaches the second reservoir 42.

As in the foregoing embodiments, a control means 51 suitably selects the on-off interval of the third laser, whereby the particles move in array with a predetermined spacing in the path 44 without mutual adhesion or overlapping of the particles.

[5th embodiment]

Figure 7:
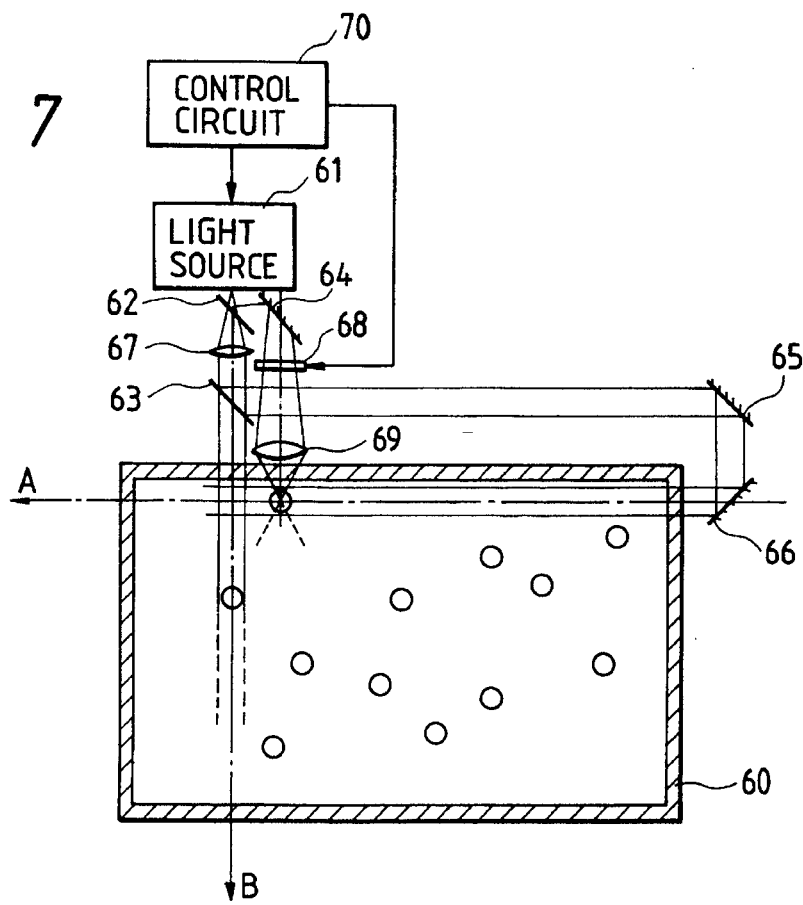
FIG. 7 is a view showing the configuration of an apparatus of a fifth embodiment.

FIG. 7 shows the configuration of an apparatus constituting a fifth embodiment, which is simplified from the configuration of the foregoing fourth embodiment. In the present embodiment, instead of the independent laser light sources in the foregoing embodiment, the light from a laser light source is split by a beam splitter into three laser beams. Also, no path is provided for guiding the moving particles.

In a container 60 the particle dispersion is sealed in a manner similar to that in the foregoing embodiments. A light source 61 is composed of a YAG laser. Among the laser beams emitted therefrom, a beam transmitted by a beam splitter 62 and a lens 67 and split by a beam splitter 63 is further reflected by mirrors 65, 66 and introduced as the first laser beam into the container 60 (direction A). A laser beam transmitted by the beam splitter 62, lens 67 and beam splitter 63 is introduced into the container 60 as the second laser beam (direction B). Also, a laser beam emitted from the light source 61 and split by the beam splitter 62 is reflected by a mirror 64, then transmitted by a shutter 68 and focused by a lens 69 as the third laser beam onto the optical axis of the first laser beam. The positional relationship of the first, second and third laser beams is similar to that in the foregoing fourth embodiment. Also, there is provided a measuring system similar to that shown in FIG. 6 in order to optically measure the fine particles moved in array in the direction B.

The spacing in transportation of the particles is determined by on-off control of the irradiation of the third laser beam for optical trapping, through switching of the shutter 68 (liquid crystal shutter or mechanical shutter) under the control of a control means 70. The shutter may also be replaced by an optical modulation element, such as an acoustooptical element.

[6th embodiment]

Generally, assuming that the intensity and the wavelength of the light for optical trapping are constant, the trapping force acting on the particle becomes larger, as the particle size increases or as the difference in refractive index between the particle and the dispersion medium becomes larger (in the case the refractive index of the particle is larger than that of the dispersion medium). Also, in the case of the same particle size, the trapping force acting thereon becomes larger, as the light intensity for optical trapping becomes stronger, or as the focused spot size of the light becomes smaller, or as the wavelength of the light becomes shorter. Consequently, the particles may be trapped or not depending on the size or the refractive index thereof. In the following there will be explained an embodiment for separating the particles, utilizing the above-explained phenomenon, according to the size or the refractive index.

Figure 8:
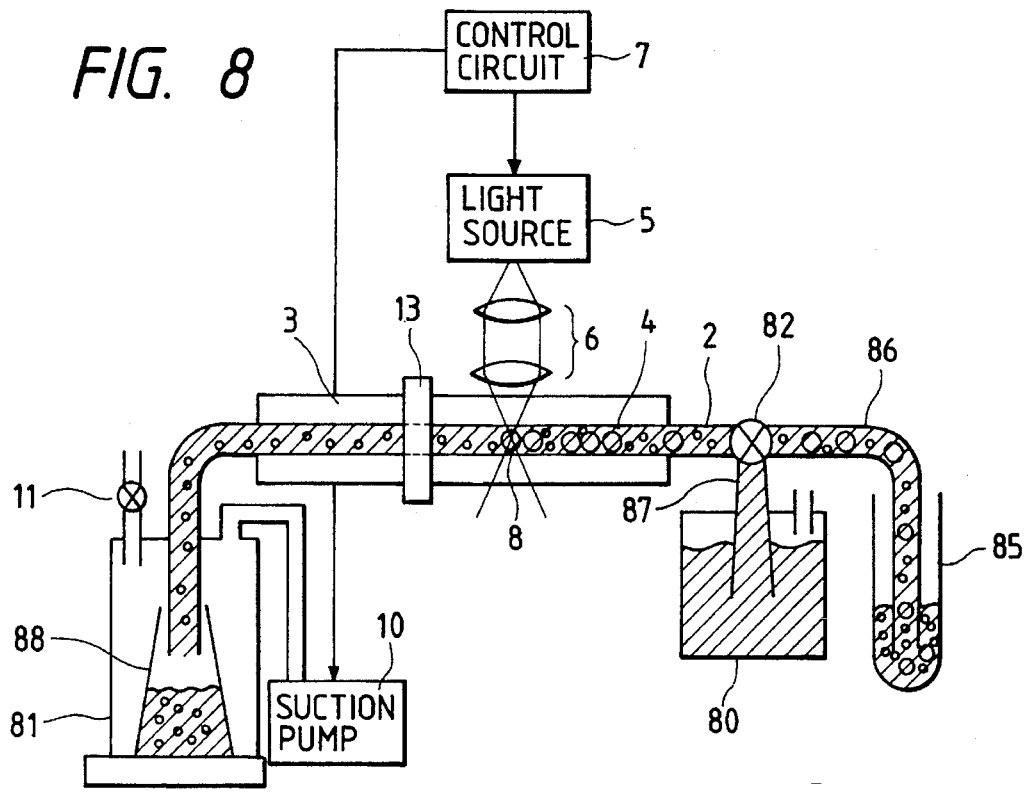
FIG. 8 is a schematic view of a sixth embodiment.

FIG. 8 illustrates the configuration of an apparatus constituting a sixth embodiment, wherein a specimen container 85 contains liquid consisting of at least two different particles and a dispersion medium (for example, water). The fine particles and dispersion medium have comparable specific gravities. In the present embodiment, the different particles are defined to be different in (1) size, (2) refractive index, or (3) size and refractive index. Examples of the fine particles include cells, viruses, microorganisms, bioparticles such as DNA or RNA, carrier particles and industrial particles.

A container 80 contains the dispersion medium (for example, water). In the specimen container 85 and the container 80, there are respectively inserted tubes 86, 87 which are connected to a flow path 2 through a joint valve 82. The flow path 2 includes a flow cell 3 of quartz glass in the middle, and is connected to a discharge chamber 81. The chamber 81 can be maintained in a hermetically sealed condition by closing a valve 11. In the discharge chamber 81 there is provided a fraction container 88, into which the liquid having passed the flow path 2 is charged. In the above-explained configuration, the interior of the discharge chamber 81 is maintained at a low pressure by the activation of a vacuum pump 10, thereby forming a flow of the dispersion medium including the fine particles, in the flow path 2. At a downstream position of the irradiation position in the flow cell 3, there is provided particle measuring means 13 utilizing, for example, an optical, electrical, magnetic or acoustooptical method.

In the apparatus of the present embodiment, in order to set a threshold value for separating the particles according to the size or the refractive index thereof, the intensity of the trapping light beam, which is emitting from a light source 5 and irradiated on the position 8, is rendered adjustable. This adjustment can be achieved, for example, by (1) controlling the emission intensity of the light source 5, (2) regulating the irradiating light amount by placing a modulation element or a filter in the optical path, or (3) regulating the practical light amount by varying the focused spot size at the irradiation position through adjustment of a lens 6.

The functions of the above-explained apparatus are as follows. At first, the joint valve 82 is connected to the tube 86 to introduce a small amount of the particle dispersion from the specimen container 85 into the flow path 2. Then, the joint valve 82 is switched to the tube 87, thereby introducing the dispersion medium only. Thus, the fine particles flow in the flow cell 3, together with the flow of the dispersion medium. In the irradiation position 8, a larger trapping force acts on a particle larger in size or in refractive index. In a control means 7, the irradiation intensity is set in advance by the above-mentioned method at such a level than the particles that are large in size (or in refractive index) are trapped but those that are small in size (or in refractive index) are not trapped. Consequently, the particles larger in size (or in refractive index) alone are trapped at the irradiation position 8, while the smaller particles pass this position. Thus, the smaller particles alone are selectively transmitted, then measured by the measuring means 13 and are charged in the fraction container 88. Thereafter, the fraction container 88 may be recovered, and the particles trapped at the irradiation position may be measured by flowing one by one through the control of the irradiation timing.

In the present embodiment, the threshold value for particle separation is set by adjusting the intensity of the irradiating light, but the threshold value may be varied by the wavelength of the irradiating light instead of the intensity.

[7th embodiment]

In the foregoing embodiment shown in FIG. 8, the particle separation is executed by trapping the particles completely at the irradiation position, but the separation may also be achieved by varying the moving velocity in such a manner that suitable braking force is applied to the particles according to the kind of the particle without complete trapping. In the following there will be explained such embodiment.

Figure 9:
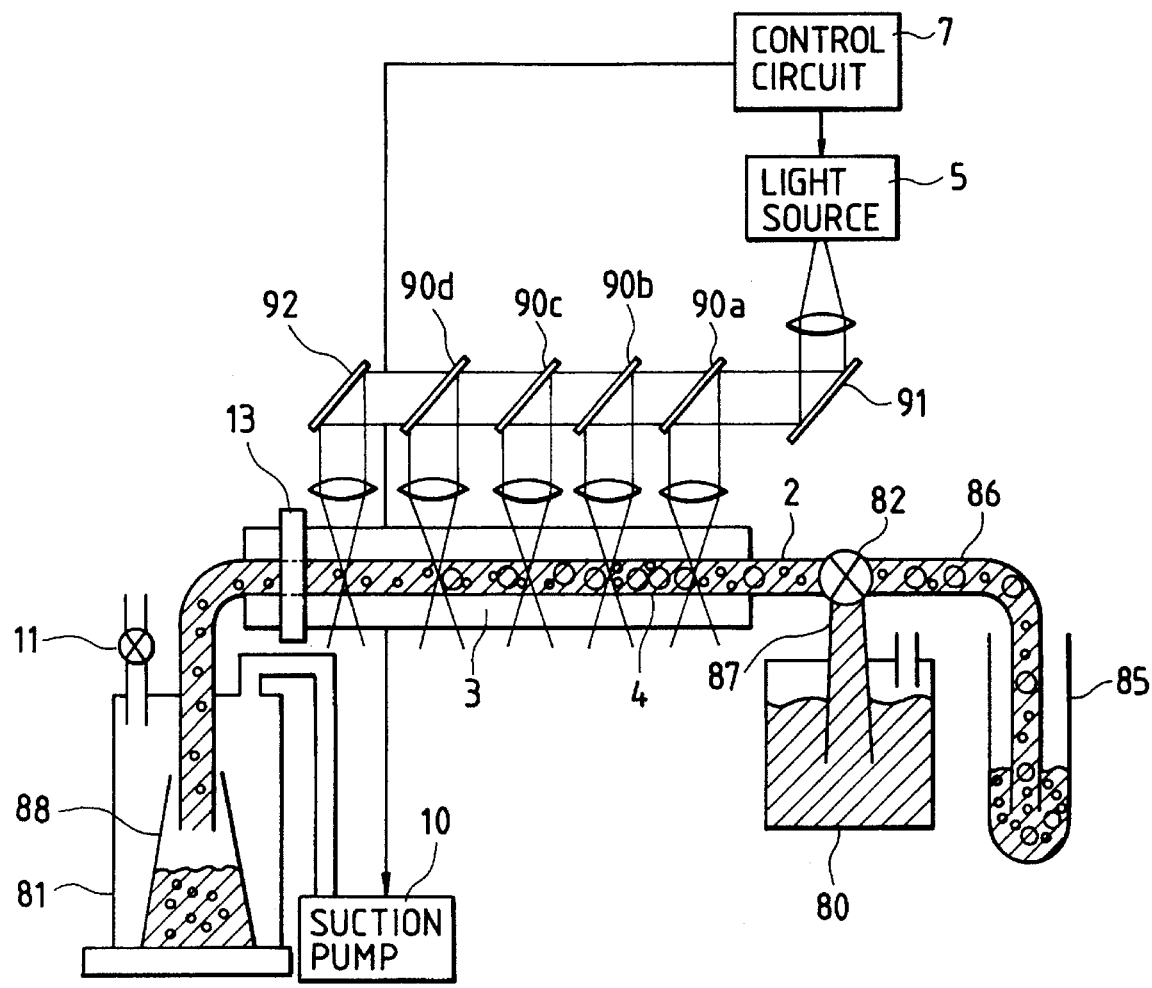
FIG. 9 is a schematic view of a seventh embodiment.

FIG. 9 illustrates the configuration of an apparatus constituting a seventh embodiment of the present invention, wherein same components as those in FIG. 8 are represented by the same numbers. The light emitted from the light source 5 is reflected by a mirror 91, and then separated into five beams by four half mirrors 90a, 90b, 90c, 90d and a mirror 92. The beams are respectively focused by lenses onto five positions along the flow in the flow cell 3. In the present embodiment, the reflectance/transmittance of the half mirrors 90a to 90d are so selected that the irradiation intensities are mutually equal at the irradiation positions. The irradiation intensity is maintained at such level as to not cause complete trapping of the particles. If necessary, the irradiation intensities may be made different at the irradiation positions. Also, the irradiation intensity may be made variable in order to vary the braking force.

In the above-explained configuration, when the fine particles of the plurality of kinds different in the size or refractive index, a particle receiving a larger trapping force becomes slower in the moving velocity, thereby receiving a larger braking force at each irradiation position. Consequently, the particles receiving the smaller braking force flow faster, and the particle separation can be achieved.

[8th embodiment]

Figure 10A:
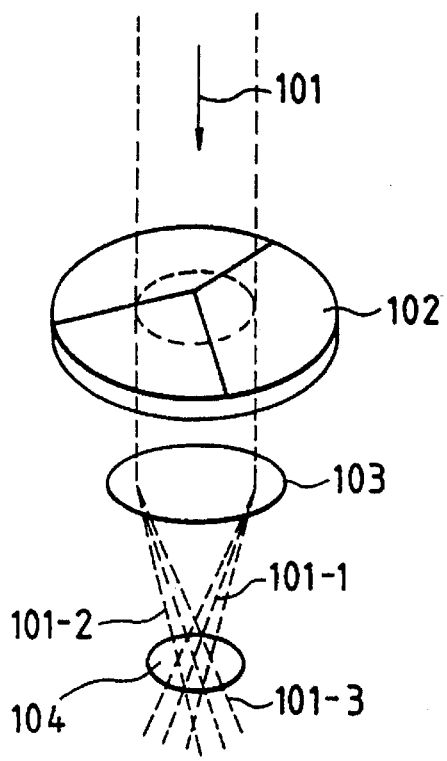
FIG. 10A and 10B are schematic views of an eighth embodiment.
Figure 10B:
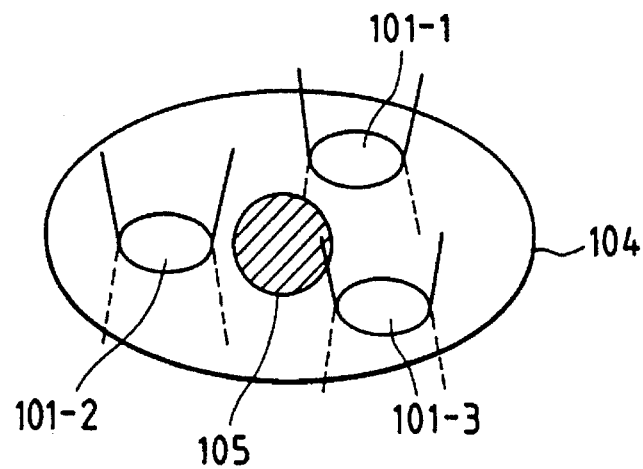

In the following there will be explained a method of trapping the fine particles in the case where they are lower in the refractive index than in the surrounding medium, or they reflect or absorb light. FIGS. 10A and 10B explain an eighth embodiment of the present invention. A laser beam 101 of Gaussian intensity distribution, emitted from an unrepresented laser light source (for example, He-Ne laser) enters an optical element 102 having a beam splitting function. The optical element 102 is shaped as a thin cylinder one of whose faces is obliquely scraped off from the center toward a condenser lens 103 to form triangular cone. By the function of the optical element 102, the incident laser beam is split into three beams, which are focused by the condenser lens 103 as three beams 101-1, 101-2, 101-3 on a focal plane 104.

In the right-hand side of FIG. 10 there is shown a magnified view of the focal plane 104. The fine particle 105 has a lower refractive index than in the surrounding medium, or reflects or absorbs the light so that the radiation pressure functions as a repulsive force. The fine particle 105 in a position surrounded by the focal positions of three laser beams 101-1, 101-2, 101-3, cannot move from this position, because even if the particle 105 is intended to be moved outside, it is pushed back since the radiation pressures of the laser beams function as repulsive forces. Therefore, the fine particle is trapped in such position surrounded by the laser beams.

[9th embodiment]

FIG. 11 is a schematic view of a ninth embodiment of the present invention, in which the fine particles can be transported by the movement of a laser beam. A laser beam emitted from a laser light source 106 enters, through an optical pickup 108, a polarization light conversion element 109 having a light splitting function, which is detailedly disclosed in Japanese Patent Laid-Open Application No. 3-191318.

The laser beam 7, entering the polarization light conversion element 109, is separated by a polarization beam splitter 109-1 into an S-wave beam (reflected) and P-wave beam (transmitted). The reflected S-beam is subjected to a slight bending of the optical axis by a wedge-shaped optical element 109-2, then transmitted by a λ/4-plate 109-3, reflected by a mirror 109-4 and again transmitted by the λ/4-plate 109-3, whereby it is converted into P-wave beam by a phase change of λ/2. This P-wave beam is transmitted by the beam splitter 109-1, then reflected by a mirror 109-5 and emerges from the lower face of the element 109. On the other hand, the P-wave beam from the incident laser beam 107 and transmitted by the beam splitter 109-1 emerges from the lower face of the element 109. These two emerging light beams are focused by a lens 110 as two beams 107-1, 107-2 on a focal plane.

In such an optical configuration, when the optical pickup 108 is moved by an unrepresented driving mechanism in a direction of arrow perpendicular to the optical axis, the two laser beams 107-1, 107-2 move as indicated by an arrow 111-1. Thus, a fine particle 105 is pushed by the repulsive force of the radiation pressure of the laser beams and can be moved as indicated by an arrow 111-2.

[10th embodiment]

FIG. 12 schematically shows a tenth embodiment of the present invention, in which the same components as those in FIG. 11 are represented by the same numbers. This embodiment is different from the configuration shown in FIG. 11 in a point that two laser light sources are used to form four beams around the fine particle. Two laser light sources 106-1, 106-2 are positioned as illustrated, and four laser beams 106-1-1, 106-1-2, 106-2-1, 106-2-2 are obtained by an optical system similar to that in FIG. 11. A fine particle 105 is trapped by these laser beams.

As the fine particle 105 in the present embodiment is trapped by the laser beams in the surrounding four positions, it can be transported in an arbitrary three-dimensional direction by a movement of the optical pickup 108 in an arbitrary direction along the optical axis or perpendicular thereto, thereby three dimensionally moving the focal positions of the laser beams. Also, the fine particle may be trapped or released arbitrarily, by the on-off control of two laser light sources 106-1, 106-2.

[11th embodiment]

In the following is explained an eleventh embodiment of the present invention. In contrast to the embodiments shown in FIGS. 10 to 12 which deal with one fine particle, the present embodiment can move two fine particles individually, so that, for example, two fine particles can be attached to each other and fused.

Figure 13:
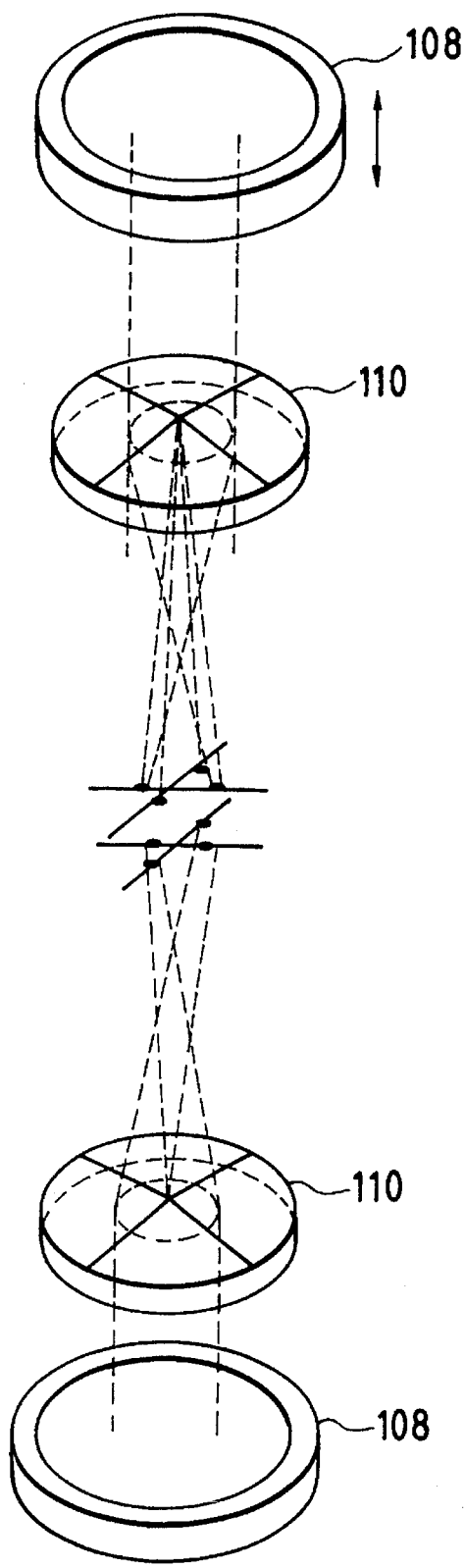
FIG. 13 is a schematic view of an eleventh embodiment.

In order to split a laser beam into four beams, there is employed an optical element 112 shaped as a quadrangular cone at a side as shown in FIG. 13, and the optical system is constructed similar to that in FIG. 10. Also, at the light source side on the optical axis, there is provided an optical pickup 108 which can be axially moved. Another similar optical system is symmetrically positioned on the optical axis as shown in FIG. 13, whereby two fine particles can be independently trapped and moved on the same optical axis.

Figure 14A:
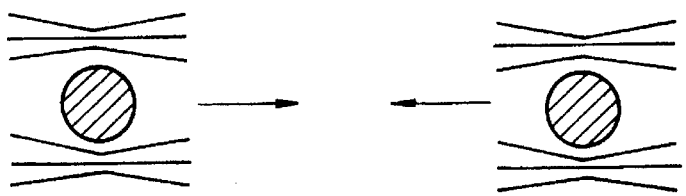
FIG. 14A and 14B are schematic views of the eleventh embodiment.
Figure 14B:
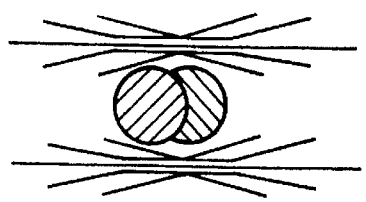

In such configuration, when the two optical pickups 108 are moved in a direction of the optical axis, the focal positions of the laser beams can be axially moved, thereby moving the fine particles trapped therein, respectively. FIGS. 14A and 14B show the mode of such movement. Two fine particles are mutually attached and fused by transferring from a state in FIG. 14A to a state in FIG. 14B.

[12th embodiment]

Figure 15:
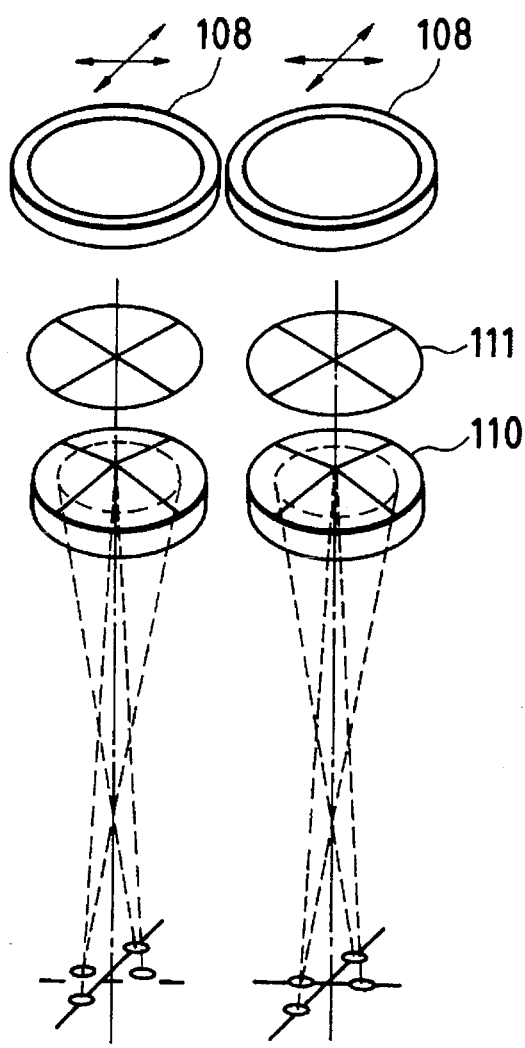
FIG. 15 is a schematic view of a twelfth embodiment.

In a twelfth embodiment of the present invention, which is explained in the following, an optical shutter 111 divided into four sectors is provided, as shown in FIG. 15, in front of a four-sectored optical element 112. The optical shutter 111 is a PLZT optical shutter, and has a circular shape split into four sectors, respectively, so as to correspond to the four faces of the quadrangular cone. It can independently turn on and off four beams on the focal plane. Two optical system of such structure are arranged side by side, as shown in FIG. 15. Each optical pickup 108 is rendered movable in a plane perpendicular to the optical axis.

Figure 16A:
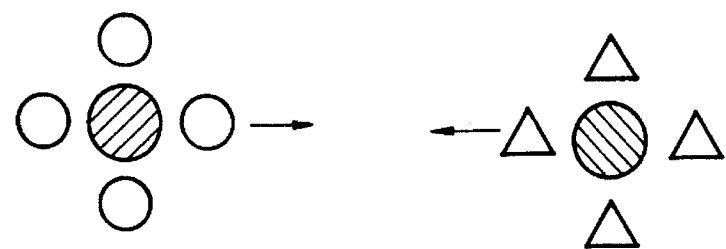
FIGS. 16A to 16C are schematic views of the twelfth embodiment.
Figure 16B:
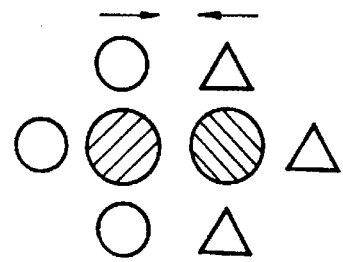
Figure 16C:
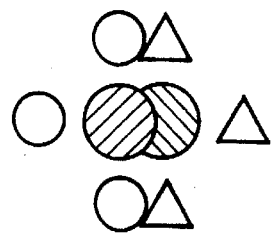

FIGS. 16A to 16C show the time-sequential control in the case of attaching of two fine particles. In a state shown in FIG. 16A, four beams are turned on around each particles and are so moved that the two particles approach each other. When the two particles are close to each other, the optical shutters 111 are so controlled as to turn off only a laser beam that is closest to the opposite particle, as shown in FIG. 16B. Thus, the two fine particles can be stably attached, as shown in FIG. 16C.

What is claimed is:

1. A particle manipulating method comprising the steps of:

flowing a plurality of particles, some of which are different in kind, along a predetermined flow path without using a sheath flow method; and irradiating a light beam, having an intensity gradient distribution, on the predetermined flow path from the direction crossing to the direction along the predetermined path to apply a braking force to each of the flowed particles, according to the kind of particle, to sort the flowed particles by reducing the flow velocity of the particle according to the kind of the particle.

2. A method according to claim 1, wherein the light beam includes a laser beam.

3. A method according to claim 1, further comprising determining the kind of the particles by at least one of a particle size and a refractive index.

4. A method according to claim 1, wherein said irradiating step comprises irradiating the light beam onto a plurality of positions along the predetermined path.

5. A method according to claim 1, further comprising a step of measuring said flowed particles.

6. A method according to claim 5, wherein said measuring step comprises optically measuring the particles.

7. A method according to claim 1, wherein said particles are biological particles.

* * * * *

UNITED STATES PATENT AND TRADEMARK OFFICE
CERTIFICATE OF CORRECTION

PATENT NO. : 5,495,105
DATED : February 27, 1996
INVENTOR(S) : MATSUOMI NISHIMURA, et al.

It is certified that error appears in the above-indentified patent and that said Letters Patent is hereby corrected as shown below:

COLUMN 1

Line 6, "08/017/390" should read --08/017,390--.

COLUMN 2

Line 1, "of a" should read --of--.
Line 2, "of" should read --of a--.
Line 11, "FIG. 10A and 10B" should read --FIGS. 10A and 10B--.
Line 16, "FIG. 14A and 14B" should read --FIGS. 14A and 14B--.
Line 60, "laser," should read --lasers,--.

COLUMN 3

Line 35, "plurality" should read --plurality of--.

COLUMN 4

Line 50, "State" should read --state--.

COLUMN 5

Line 48, "of" should read --of the--.
Line 63, "149" should read --49--.

UNITED STATES PATENT AND TRADEMARK OFFICE
CERTIFICATE OF CORRECTION

PATENT NO. : 5,495,105

DATED : February 27, 1996

INVENTOR(S) : MATSUOMI NISHIMURA, et al.

It is certified that error appears in the above-indentified patent and that said Letters Patent is hereby corrected as shown below:

<u>COLUMN 8</u>

Line 66, "in the" should read --in--.

<u>COLUMN 10</u>

Line 61, "system" should read --systems--.

<u>COLUMN 11</u>

Line 1, "particles" should read --particle--.

Signed and Sealed this

Fifth Day of November, 1996

BRUCE LEHMAN

Attest:

Attesting Officer    Commissioner of Patents and Trademarks